(12) United States Patent
Bellerose et al.

(10) Patent No.: US 8,556,115 B2
(45) Date of Patent: Oct. 15, 2013

(54) SURGICAL INSTRUMENT CONTAINER ASSEMBLY WITH ELLIPTICAL SOFTGRIP HANDLE ASSEMBLY

(75) Inventors: Jean E Bellerose, Hillsboro, NH (US); Valentine T. Faust, III, Bow, NH (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 1480 days.

(21) Appl. No.: 11/103,875

(22) Filed: Apr. 12, 2005

(65) Prior Publication Data

US 2006/0118444 A1 Jun. 8, 2006

Related U.S. Application Data

(63) Continuation-in-part of application No. 29/218,413, filed on Dec. 2, 2004.

(51) Int. Cl.
*B65D 71/52* (2006.01)

(52) U.S. Cl.
USPC ........... 220/755; 206/557; 206/368; 220/761; 220/757; 220/763

(58) Field of Classification Search
USPC .......... 206/363, 364, 375, 368, 557; 220/570, 220/754, 757, 758–760, 765, 769, 755, 761, 220/763, 766
See application file for complete search history.

(56) References Cited

U.S. PATENT DOCUMENTS

| | | | |
|---|---|---|---|
| 293,752 A * | 2/1884 | Krahenbeihl et al. ........ | 138/145 |
| 616,746 A * | 12/1898 | Taylor ......................... | 74/558.5 |
| 1,980,655 A * | 11/1934 | Balistreri ..................... | 15/143.1 |
| 2,655,963 A * | 10/1953 | Dell ............................. | 81/492 |
| 2,984,486 A * | 5/1961 | Jones .......................... | 473/568 |
| 3,072,955 A * | 1/1963 | Mitchell ...................... | 294/171 |
| 3,606,218 A * | 9/1971 | Enlund et al. ............... | 248/74.2 |
| 3,619,852 A * | 11/1971 | Mitchell ...................... | 16/425 |
| 4,098,506 A * | 7/1978 | Gaiser ......................... | 473/538 |
| 4,197,611 A * | 4/1980 | Bell et al. .................... | 220/753 |
| 4,867,444 A * | 9/1989 | Castillo ....................... | 482/106 |
| 4,890,355 A * | 1/1990 | Schulten ...................... | 16/421 |
| 4,941,232 A | 7/1990 | Decker et al. ................ | 16/111 |
| 5,042,804 A * | 8/1991 | Uke et al. .................... | 473/538 |
| 5,064,203 A * | 11/1991 | Hattori ........................ | 473/551 |
| 5,083,825 A * | 1/1992 | Bystrom et al. ............. | 294/171 |
| 5,088,733 A * | 2/1992 | Barnea et al. ................ | 473/568 |
| 5,097,566 A | 3/1992 | Decker et al. ................ | 16/111 |
| 5,098,752 A * | 3/1992 | Chang et al. ................. | 428/34.9 |
| 5,134,008 A | 7/1992 | Alm ............................. | 428/90 |
| 5,160,105 A * | 11/1992 | Miller ......................... | 248/188.9 |
| 5,339,955 A * | 8/1994 | Horan et al. ................. | 206/370 |
| D360,346 S * | 7/1995 | Huttner ....................... | D8/321 |
| 5,472,111 A * | 12/1995 | Renfrew ...................... | 220/570 |
| 5,511,445 A * | 4/1996 | Hildebrandt ................. | 74/558.5 |
| 5,538,245 A * | 7/1996 | Moore ......................... | 473/239 |
| 5,664,520 A * | 9/1997 | Latimer, III .................. | 16/421 |

(Continued)

*Primary Examiner* — Anthony Stashick
*Assistant Examiner* — Christopher McKinley
(74) *Attorney, Agent, or Firm* — Taylor IP, P.C.

(57) ABSTRACT

A surgical instrument container assembly includes a container and a handle assembly. The handle assembly includes at least one wire handle pivotally coupled with the container. A handle grip has a longitudinally extending opening. A portion of the wire handle is positioned radially within the opening. The handle grip has an outer surface with an elliptical cross sectional shape, and a plurality of laterally spaced and longitudinally extending ribs on the outer surface. The handle grip is preferably formed of an elastomeric material.

18 Claims, 4 Drawing Sheets

(56) References Cited

U.S. PATENT DOCUMENTS

| | | | |
|---|---|---|---|
| 5,860,190 A * | 1/1999 | Cano | 16/422 |
| 5,890,260 A * | 4/1999 | Gaunt | 16/436 |
| 5,926,912 A * | 7/1999 | Claphan | 16/411 |
| 5,944,617 A * | 8/1999 | Falone et al. | 473/300 |
| 5,950,280 A * | 9/1999 | Taylor | 16/422 |
| 6,006,403 A | 12/1999 | Battiato | 16/421 |
| 6,062,389 A * | 5/2000 | Kent | 206/518 |
| D429,454 S * | 8/2000 | Lademann, III | D8/303 |
| 6,096,254 A * | 8/2000 | Nielsen | 264/237 |
| 6,154,928 A * | 12/2000 | Thom | 16/413 |
| 6,235,134 B1 | 5/2001 | Mueller | 156/83 |
| 6,719,342 B2 * | 4/2004 | Shinmoto et al. | 294/171 |
| 6,976,405 B2 * | 12/2005 | Schaeffer | 81/3.55 |
| 7,065,883 B2 * | 6/2006 | Popeil et al. | 30/322 |
| 7,141,197 B2 * | 11/2006 | Chadwick et al. | 264/250 |
| 7,150,685 B1 * | 12/2006 | Berokoff | 473/294 |

* cited by examiner

SURGICAL INSTRUMENT CONTAINER ASSEMBLY WITH ELLIPTICAL SOFTGRIP HANDLE ASSEMBLY

CROSS REFERENCE TO RELATED APPLICATIONS

This is a continuation-in-part of U.S. Design patent application Ser. No. 29/218,413, entitled "ELLIPTICAL SOFT GRIP HANDLE", filed Dec. 2, 2004.

BACKGROUND OF THE INVENTION

1. Field of the Invention

The present invention relates to surgical instrument cases, and, more particularly, to handle assemblies for such cases.

2. Description of the Related Art

Surgical instrument containers are known that provide organization, storage and sterilization functionality for surgical instruments and devices. Surgical procedures are regularly performed using "sets" of pre-selected surgical instruments, each set being a collection of instruments established from experience or design to be useful in a given surgical procedure. The surgical instruments expected to be used in a particular procedure are grouped together to form a set, and, as a set, are arranged in a tray or case, sterilized, and transported to the operating room for subsequent use. Complex procedures typically involve a substantial number of instruments. Thus, typically, several instrument trays may be necessary to accommodate all of the required surgical instruments. Accordingly, sterilizing cases often are designed to accommodate a plurality of trays with the instruments arranged on the trays in such a manner that the trays may be accessed as the surgical procedure advances, often in a preset sequence.

To assist in transport and use, the trays and/or cases may include one or more handles which are grasped by a user. The handles may be located on the sides or top of the tray and/or case. Such handles may be in the form of, e.g., a simple wire handle allowing a user to open, move and/or transport the tray and/or case. Although such handles are functional, they tend not to be particularly ergonomic and/or easy to use.

What is needed in the art is a handle assembly for a surgical container which is easier to use, non-obtrusive, and ergonomically designed.

SUMMARY OF THE INVENTION

The present invention provides a handle assembly for a surgical instrument container with an elliptical softgrip handle which is ergonomically designed and folds flat against the container for stacking.

The invention comprises, in one form thereof, a surgical instrument container assembly, including a container and a handle assembly. The handle assembly includes at least one wire handle pivotally coupled with the container. A handle grip has a longitudinally extending opening. A portion of the wire handle is positioned radially within the opening. The handle grip has an outer surface with an elliptical cross sectional shape, and a plurality of laterally spaced and longitudinally extending ribs on the outer surface. The handle grip is preferably formed of an elastomeric material.

An advantage of the present invention is that the handle is formed from an elastomeric material providing comfortable and slip free gripping.

Another advantage is that the longitudinally extending ribs on the outer surface provide further increased comfort and slip free gripping.

Yet another advantage is that the elliptical shape of the handle provides ergonomic gripping when in use, and allows the handle grip to be folded flat against the container when not in use.

Still another advantage is that the ribs at the inner longitudinally extending opening in the handle grip allow the handle grip to be simply slid over the inner tube during manufacture, and frictionally engage the tube.

Yet another advantage is that the handle grip can be manufactured using a simple extrusion or injection molding process.

Still another advantage is that the wire handle can be manufactured with a one piece or two piece design.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 8:
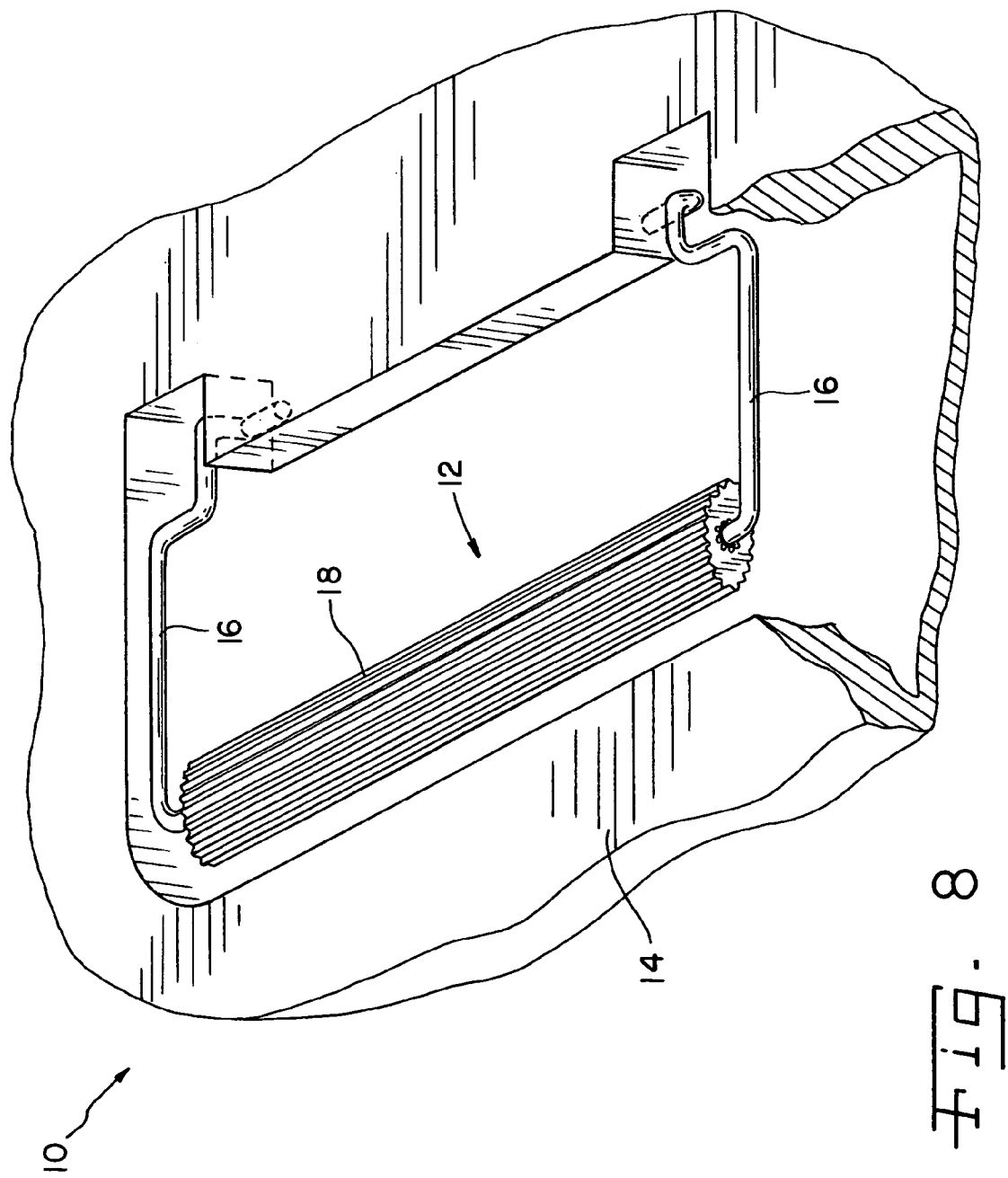
FIG. 8 is a perspective view of the handle assembly shown in FIGS. 1-7, pivotally coupled to a portion of a surgical instrument container.

Referring now to the drawings, there is shown an embodiment of a surgical instrument container assembly 10, which generally includes a handle assembly 12 which is attached to a container 14 (FIG. 8). Container 14 is in the form of a tray for orthopaedic instruments in the embodiment shown, but may also be in the form of a drawer, case, etc. for orthopaedic instruments.

Handle assembly 12 includes a wire handle 16 and handle grip 18. Wire handle 16 is pivotally coupled with container 14. Although shown as a single wire design, wire handle 16 may also be configured as a split wire rather than a single wire.

Figure 1:
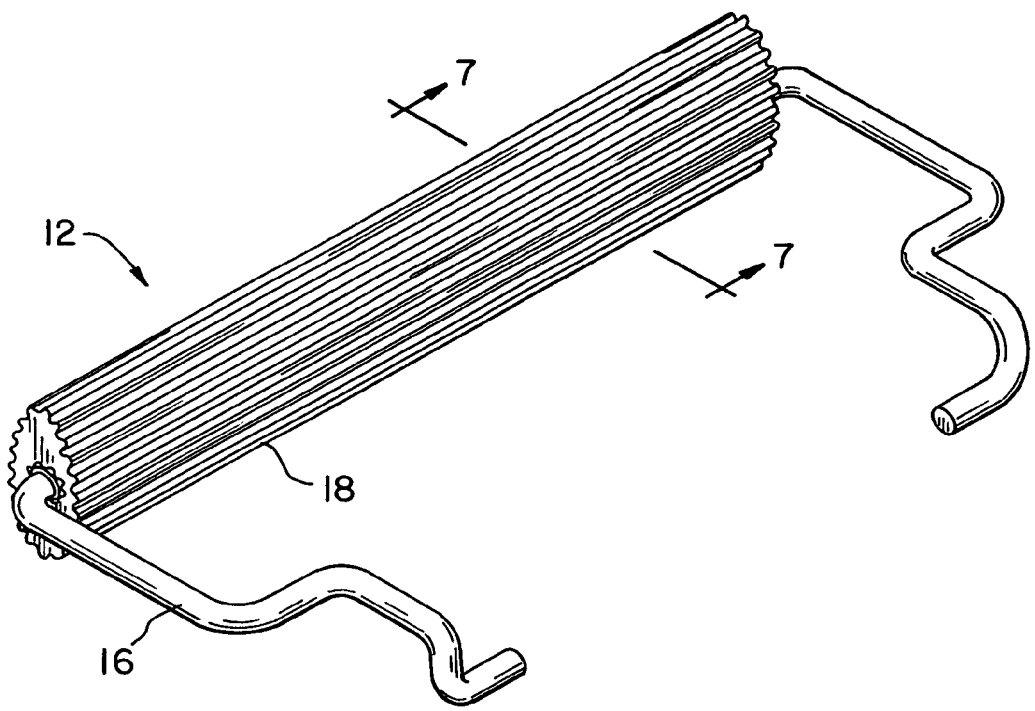
FIG. 1 is a perspective view of an embodiment of a handle assembly of the present invention used in conjunction with a surgical instrument container.
Figure 2:
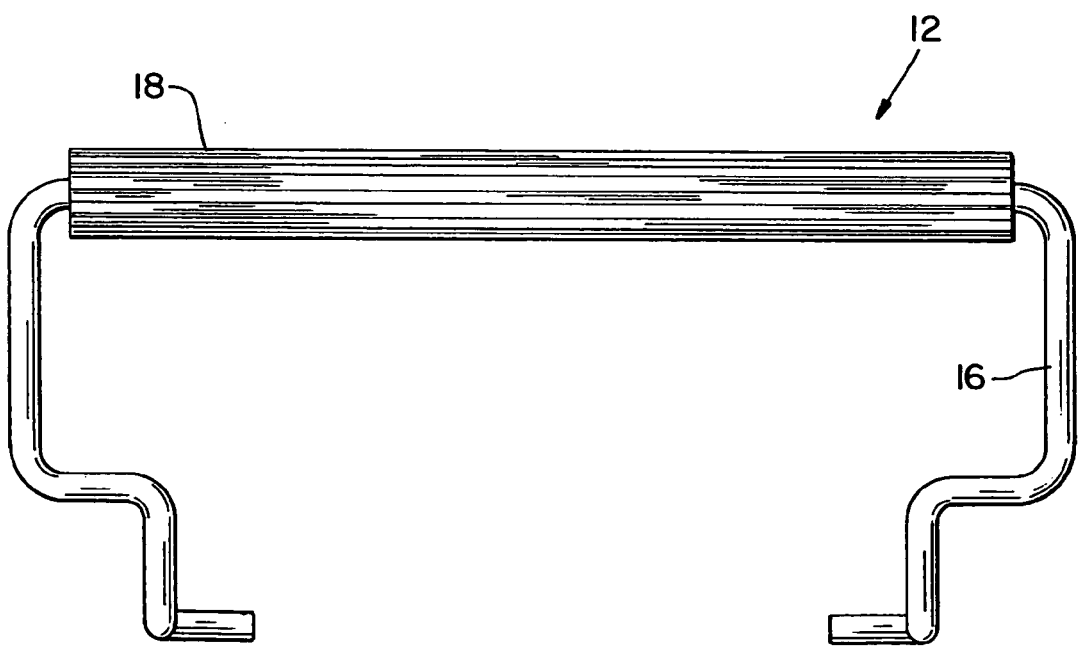
FIG. 2 is a front view of the handle assembly of FIG. 1.
Figure 3:
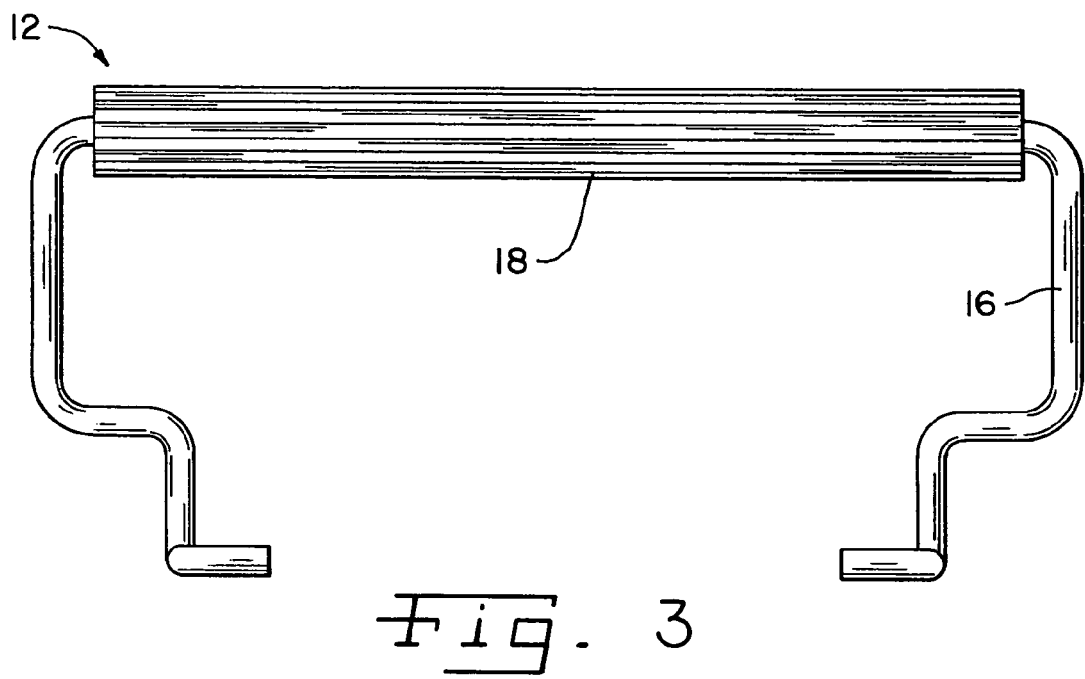
FIG. 3 is a rear view of the handle assembly shown in FIGS. 1 and 2.
Figure 4:
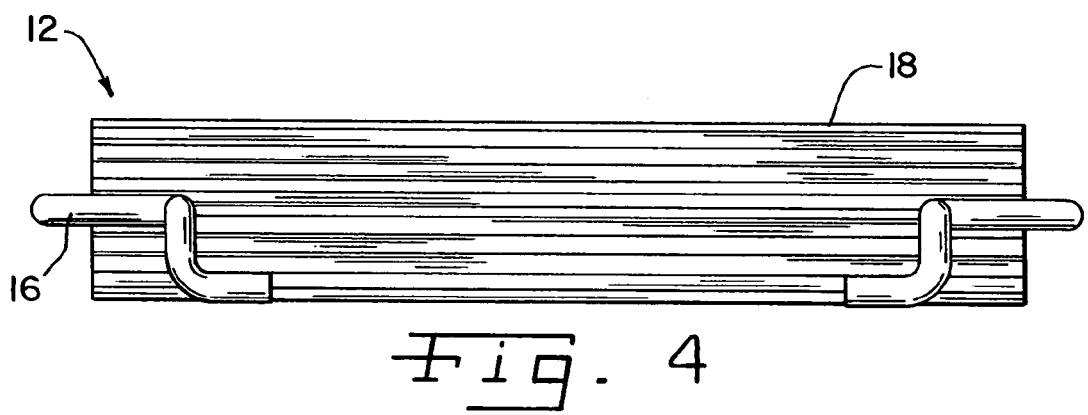
FIG. 4 is a bottom view of the handle assembly shown in FIGS. 1-3.
Figure 5:
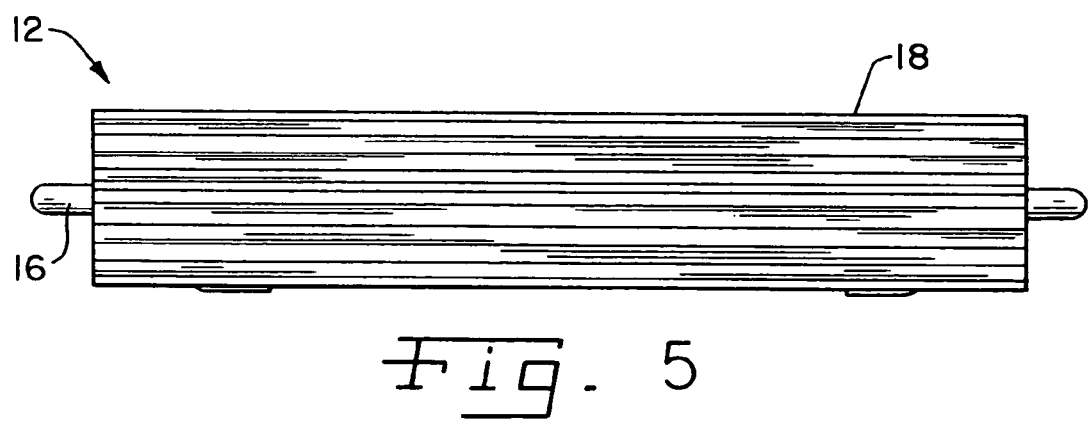
FIG. 5 is a top view of the handle assembly shown in FIGS. 1-4.
Figure 6:
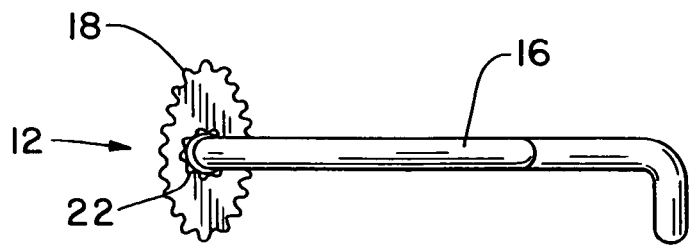
FIG. 6 is an end view of the handle assembly shown in FIGS. 1-5, the opposite end view being substantially identical.
Figure 7:
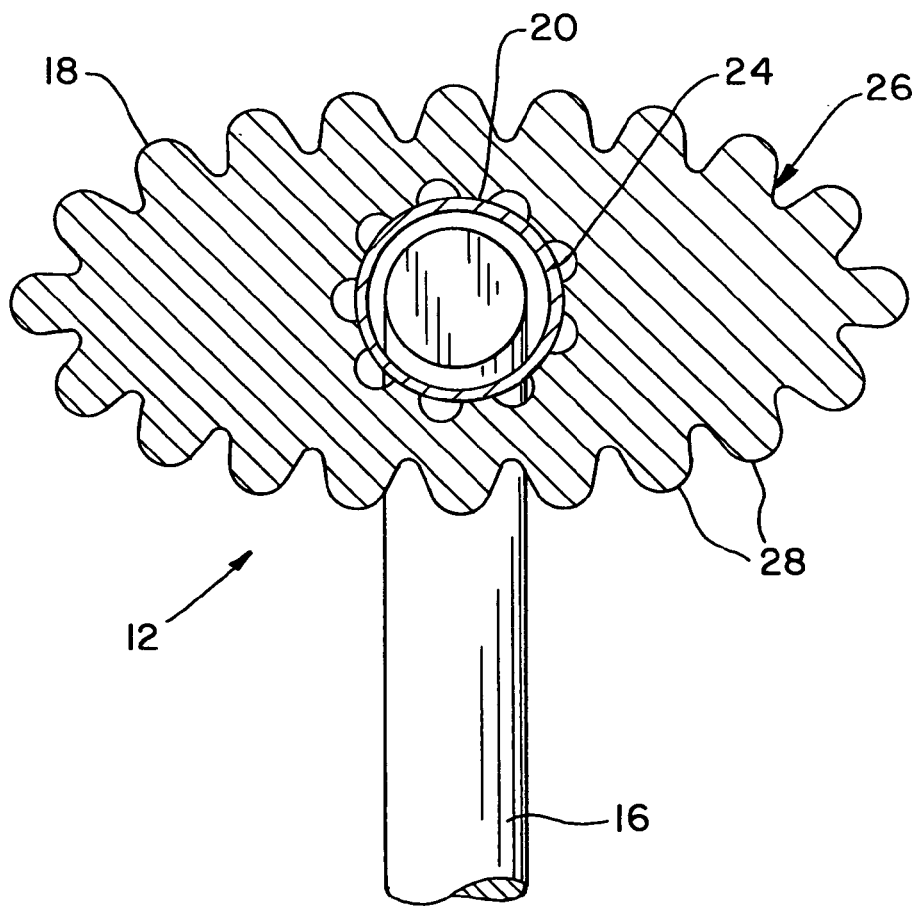
FIG. 7 is a sectional end view, taken along line 7-7 in FIG. 1.

Handle grip 18 has a longitudinally extending opening 20 (FIG. 7). A portion of wire handle 16 is positioned radially within opening 20. More particularly, longitudinally extending opening 20 includes a plurality of longitudinally extending ribs 22. A tube 24 having a length approximately the same as handle grip 18 is press fit within and frictionally engages longitudinally extending ribs 22 in opening 20. Alternatively, handle grip 18 may be overmolded around tube 24. Tube 24 is preferably a metal tube, but may also be formed of another suitable material, such as a suitable plastic. Tube 24 is freely rotatable around a portion of wire handle 16.

Handle grip 18 has an outer surface 26 with an elliptical cross sectional shape, and a plurality of laterally spaced and longitudinally extending ribs 28 on outer surface 26. Handle grip 18 is preferably formed from an elastomeric material, which in conjunction with ribs 28 provides ergonomically comfortable and slip free gripping.

During use, handle grip 18 is grasped by a user and pivoted such that wire handle 16 is approximately perpendicular to an attached wall of container 14 (provided by the bent, right angle stops at each end of wire handle 16). The elliptical cross sectional shape of handle grip 18 provides comfortable and secure gripping. When not in use, handle grip 18 is folded against the attached wall of container 14. The long cross sectional axis of handle grip 18 is placed generally parallel to the attached wall of container 14 (FIG. 8), such that handle grip 18 has a lower projected profile providing easier stacking of containers 14. A short cross sectional axis is perpendicular to the long cross sectional axis and is shorter than the long cross sectional axis.

During use, handle grip 18 is grasped by a user and pivoted such that wire handle 16 is approximately perpendicular to an attached wall of container 14 (provided by the bent, right angle stops at each end of wire handle 16). The elliptical cross sectional shape of handle grip 18 provides comfortable and secure gripping. When not in use, handle grip 18 is folded against the attached wall of container 14. The long cross sectional axis of handle grip 18 is placed generally parallel to the attached wall of container 14 (FIG. 8), such that handle grip 18 has a lower projected profile providing easier stacking of containers 14.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical instrument container assembly, comprising:
   a container having a flat wall; and
   a handle assembly, including:
      at least one wire handle coupled with said container; and
      a handle grip having a longitudinally extending opening in which a portion of said wire handle is positioned radially within, said handle grip having an outer surface with a continuous elliptical cross sectional shape having a long cross sectional axis and a short cross sectional axis that is perpendicular and shorter than said long cross sectional axis, and a plurality of laterally spaced and longitudinally extending ribs on said outer surface, said longitudinally extending opening including a plurality of longitudinally extending ribs said long cross sectional axis of said handle grip being configured to be placed generally parallel to said flat wall.

2. The surgical instrument container assembly of claim 1, further including a tube positioned radially within and frictionally engaging said longitudinally extending ribs in said opening.

3. The surgical instrument container assembly of claim 2, wherein said tube is a metal tube.

4. The surgical instrument container assembly of claim 2, wherein said tube is freely rotatable around said portion of said wire handle.

5. The surgical instrument container assembly of claim 1, further including a tube positioned radially within said longitudinally extending opening.

6. The surgical instrument container assembly of claim 5, wherein said tube is one of press fit within and overmolded within said opening.

7. The surgical instrument container assembly of claim 5, wherein said tube is freely rotatable around said portion of said wire handle.

8. The surgical instrument container assembly of claim 1, wherein said handle grip is comprised of an elastomeric material.

9. The surgical instrument container assembly of claim 1, wherein said at least one wire handle comprises a single wire handle.

10. The surgical instrument container assembly of claim 1, wherein said at least one wire handle is pivotally attached to said container.

11. The surgical instrument container assembly of claim 1, wherein said container comprises one of a tray and a case.

12. A handle assembly for a surgical instrument container, at least one wire handle attachable with said container, said container having a flat wall; and
   a handle grip having a longitudinally extending opening in which a portion of said wire handle is positioned radially within, said handle grip having an outer surface with a continuous elliptical cross sectional shape having a long cross sectional axis and a short cross sectional axis that is perpendicular and shorter than said long cross sectional axis, and a plurality of laterally spaced and longitudinally extending ribs on said outer surface, said longitudinally extending opening including a plurality of longitudinally extending ribs said long cross sectional axis of said handle grip being configured to be placed generally parallel to said flat wall.

13. The handle assembly of claim 12, further including a tube positioned radially within and frictionally engaging said longitudinally extending ribs in said opening.

14. The handle assembly of claim 13, wherein said tube is freely rotatable around said portion of said wire handle.

15. The handle assembly of claim 12, further including a tube positioned radially within and frictionally engaging said longitudinally extending opening.

16. The handle assembly of claim 15, wherein said tube is freely rotatable around said portion of said wire handle.

17. The handle assembly of claim 12, wherein said handle grip is comprised of an elastomeric material.

18. The handle assembly of claim 12, wherein said at least one wire handle comprises a single wire handle.

* * * * *

UNITED STATES PATENT AND TRADEMARK OFFICE
CERTIFICATE OF CORRECTION

PATENT NO.       : 8,556,115 B2
APPLICATION NO.  : 11/103875
DATED            : October 15, 2013
INVENTOR(S)      : Jean E. Bellerose et al.

Page 1 of 1

It is certified that error appears in the above-identified patent and that said Letters Patent is hereby corrected as shown below:

In the Specification

COLUMN 3
  Line 14 insert the following as a new paragraph before the paragraph beginning on line 15:
  --During manufacture, handle grip 18 may be formed from an elastomeric material using an
    extrusion or injection molding process. Handle grip 18 is then slid over tube 24 and inner
    ribs 22 frictionally engage tube 24. Wire handle 16 is placed within tube 24 and freely
    rotates within tube 24. Wire handle 24 then is pivotally coupled with container 14.--; and Delete the paragraph starting on line 28 and ending on line 38.

In the Claims

COLUMN 4
  Line 33, Claim 12, after "container,", insert --comprising:--.

Signed and Sealed this
Thirteenth Day of January, 2015

Michelle K. Lee
*Deputy Director of the United States Patent and Trademark Office*